United States Patent [19]

Tesberg

[11] 3,960,159

[45] June 1, 1976

[54] DENTAL FLOSS HOLDER AND APPLICATOR

[75] Inventor: Allan V. Tesberg, Daly City, Calif.

[73] Assignee: Lawrence Peska Assoc. Inc., New York, N.Y. ; a part interest

[22] Filed: Nov. 11, 1974

[21] Appl. No.: 522,737

[52] U.S. Cl. .................................................. 132/90
[51] Int. Cl.² ......................................... A61C 15/00
[58] Field of Search .................. 132/92, 92 A, 92 R, 132/91

[56] References Cited
UNITED STATES PATENTS

| | | |
|---|---|---|
| 1,217,779 | 2/1917 | Kleckner .......................... 132/92 A |
| 1,445,009 | 2/1923 | Eby .................................. 132/92 A |
| 1,733,631 | 10/1929 | Spiegel et al. ..................... 132/92 R |
| 2,289,625 | 7/1942 | Burns .................................. 132/92 |
| 2,664,093 | 12/1953 | Carpenter ............................ 132/91 |

Primary Examiner—G. E. McNeill
Attorney, Agent, or Firm—Jack D. Slobod

[57] ABSTRACT

Apparatus for holding and storing a spool of dental floss includes first and second generally planar arms mounted on a handle. Each of the arms include first and second sections fixed to each other at an angle which is greater than 90°.

3 Claims, 3 Drawing Figures

DENTAL FLOSS HOLDER AND APPLICATOR

BACKGROUND OF THE INVENTION

The invention relates to apparatus for dispensing and holding dental floss while it is being used. The prior art includes structures for dispensing and holding dental floss. One such structure is shown in Stiles, U.S. Pat. No. 3,378,017 issued Apr. 16, 1968. Other relevant United States Patents are Ness, U.S. Pat. No. 2,742,047; Lew, U.S. Pat. No. 2,962,033; Foster, U.S. Pat. No. 3,311,116; Ford, U.S. Pat. No. 3,327,719. Such patents indicate a longfelt need for apparatus which is truly simple to manufacture and easy to use. The prior art apparatus has not satisfied the demand for such structures.

Accordingly, it is a primary object of the invention to provide apparatus for dispensing and holding dental floss which is simple and inexpensive to manufacture and simple to use.

SUMMARY OF THE INVENTION

It has now been found that these and other objects of the invention may be satisfied by apparatus for dispensing and holding dental floss which comprises first and second generally planar arms, each of said arms including a first section and a second section, said sections being fixedly joined with an included angle greater than 90°; a handle is fixedly engaged to said arms to hold them in substantially parallel relationship; and said arms carry a length of dental floss along the lengths thereof between the ends thereof most remote from said handle.

Normally the arms will include anchors for the floss proximate to the handles and slots at the other end thereof together with guide rings therebetween. The anchors normally are bosses which extend substantially perpendicular to the first section of each of the arms and each boss has a slot extending generally axially through a diameter of the boss. Means for cutting the floss may be carried on the handle. The angles between the first and second sections of the arms preferably are approximately 135°.

BRIEF DESCRIPTION OF THE DRAWING

The invention will be better understood by reference to the accompanying drawing in which.

DESCRIPTION OF THE PREFERRED EMBODIMENT

Figure 1:
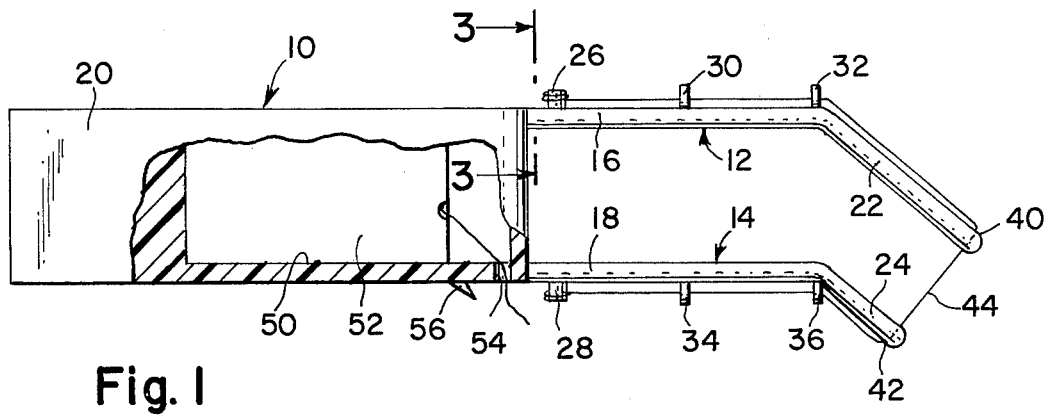
FIG. 1 is a side elevational view in partial section of the apparatus in accordance with the invention.
Figure 2:
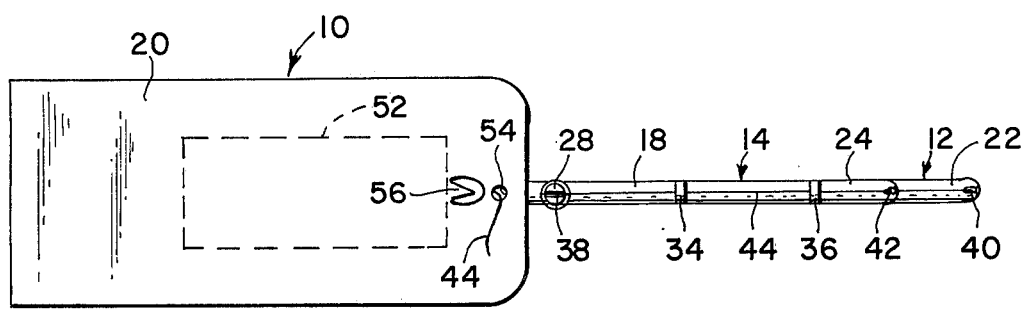
FIG. 2 is a bottom view of the apparatus shown in FIG. 1.
Figure 3:
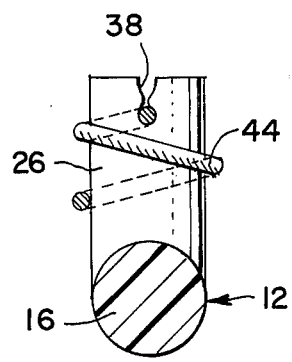
FIG. 3 is a sectional view taken through the line 3—3 of FIG. 1.

Referring now to FIGS. 1 through 3 there is shown the dental floss dispenser and holder 10 in accordance with the invention. The apparatus 10 includes arms 12, 14 which are disposed in generally parallel relationship and which each comprise first sections indicated generally by the numerals 16, 18. The first sections 16, 18 are carried in generally parallel relationship to a handle 20. Second sections indicated that generally by the numerals 22, 24 are carried in fixed relationship to the first section 16, 18. Carried on the outboard surfaces of the arm 12, 14 are respectively anchors 26, 28, guide rings 30, 32 and 34, 36. As is best shown in figure the anchors 26, 28 extend substantially perpendicular to the arms 12, 14 on which they are mounted and are provided with a slot 38 which extends axially through a diameter thereof. The slot has a gradually reduced width for firmly gripping a piece of dental floss. The guide rings 30 through 36 are provided with an opening therethrough for directing the dental floss. At the end of each arm 12, 14 is positioned a slot 40, 42 for carrying the dental floss which is designated by the numeral 44.

The handle 20 is provided with a hollow interior section 50 for carrying a floss container 52 and has an opening 54 for selective passage of the floss 44 out of the interior thereof. A cutter 56 is carried on the bottom face of the handle 20. It will be seen that the apparatus so described is easy to use and avoids the use of other clumsy apparatus which may be available and the messy use of the fingers.

Having thus described my invention, I claim:

1. Apparatus for dispensing and holding dental floss which comprises: an elongated handle configured for carrying a supply of dental floss, a pair of bent co-planar arms extending fixedly from said handle in spaced apart relationship; said arms respectively formed of elongated generally parallel first sections fixedly joined to said handle and elongated generally parallel second sections fixedly joined to said first sections and making an included angle with said first sections of greater than 90° but less than 180°, means for anchoring opposite ends of a length of said dental floss to said arms comprising generally cylindrical bosses extending substantially perpendicular to the first sections of said arms, each of said bosses having a slot extending along a diameter of said boss, said slot being configured for capturing said dental floss, and means carried by said arms for guiding said length of floss from said anchoring means along said arms and between the free ends thereof, said guiding means including slots formed at the free ends of said arms.

2. The apparatus as described in claim 1 further including means for cutting said floss carried on said handle.

3. The apparatus as described in claim 2 wherein said included angle is approximately 135°.

* * * * *